(12) United States Patent
Thorne et al.

(10) Patent No.: US 6,296,637 B1
(45) Date of Patent: Oct. 2, 2001

(54) ELECTROSURGICAL ELECTRODE AND METHODS FOR ITS USE

(75) Inventors: Jonathan O. Thorne, Boulder, CO (US); Jason Safabash, Redwood City, CA (US); James Brassell; Scott Allan Miller, III, both of Boulder, CO (US); Jeff Rondinone, Los Gatos, CA (US)

(73) Assignee: Link Technology, Inc., Boulder, CO (US)

( * ) Notice: Subject to any disclaimer, the term of this patent is extended or adjusted under 35 U.S.C. 154(b) by 0 days.

(21) Appl. No.: 09/086,613

(22) Filed: May 28, 1998

Related U.S. Application Data

(60) Provisional application No. 60/047,922, filed on May 29, 1997.

(51) Int. Cl.⁷ .................................................. A61B 18/14
(52) U.S. Cl. .................................................. 606/41; 606/49
(58) Field of Search .................................. 606/41, 45, 46, 606/49, 50

(56) References Cited

U.S. PATENT DOCUMENTS 4,593,691 * 6/1986 Lindstrom et al. ..................... 606/49
5,382,247 * 1/1995 Cimino et al. ......................... 606/45

* cited by examiner

*Primary Examiner*—Lee Cohen
(74) *Attorney, Agent, or Firm*—F. A. Sirr; E. C. Hancock; Holland & Hart LLP

(57) ABSTRACT

An electrosurgical electrode having a distal end for transferring the energy to the tissue and a thermal reservoir spaced apart from the distal end. The materials and shape of the electrode promote the flow of heat away from the distal tip so as to reduce the temperature of the tip during electrosurgery, to reduce tissue damage and to prevent the tissue from sticking to the electrode tip. The electrode is composed of a bio-compatible and highly thermally conductive metal, such as silver or gold of high purity, or alloy of those two metals. The shape provides a cross-sectional area that is constant or increasing as the distance from the tip increases. The rounded distal end transitions into a cylindrical section which then transitions into the thermal reservoir. The thermal reservoir is also cylindrical, having a cross-sectional area that is larger than the cross-sectional area of the first cylindrical section.

18 Claims, 4 Drawing Sheets

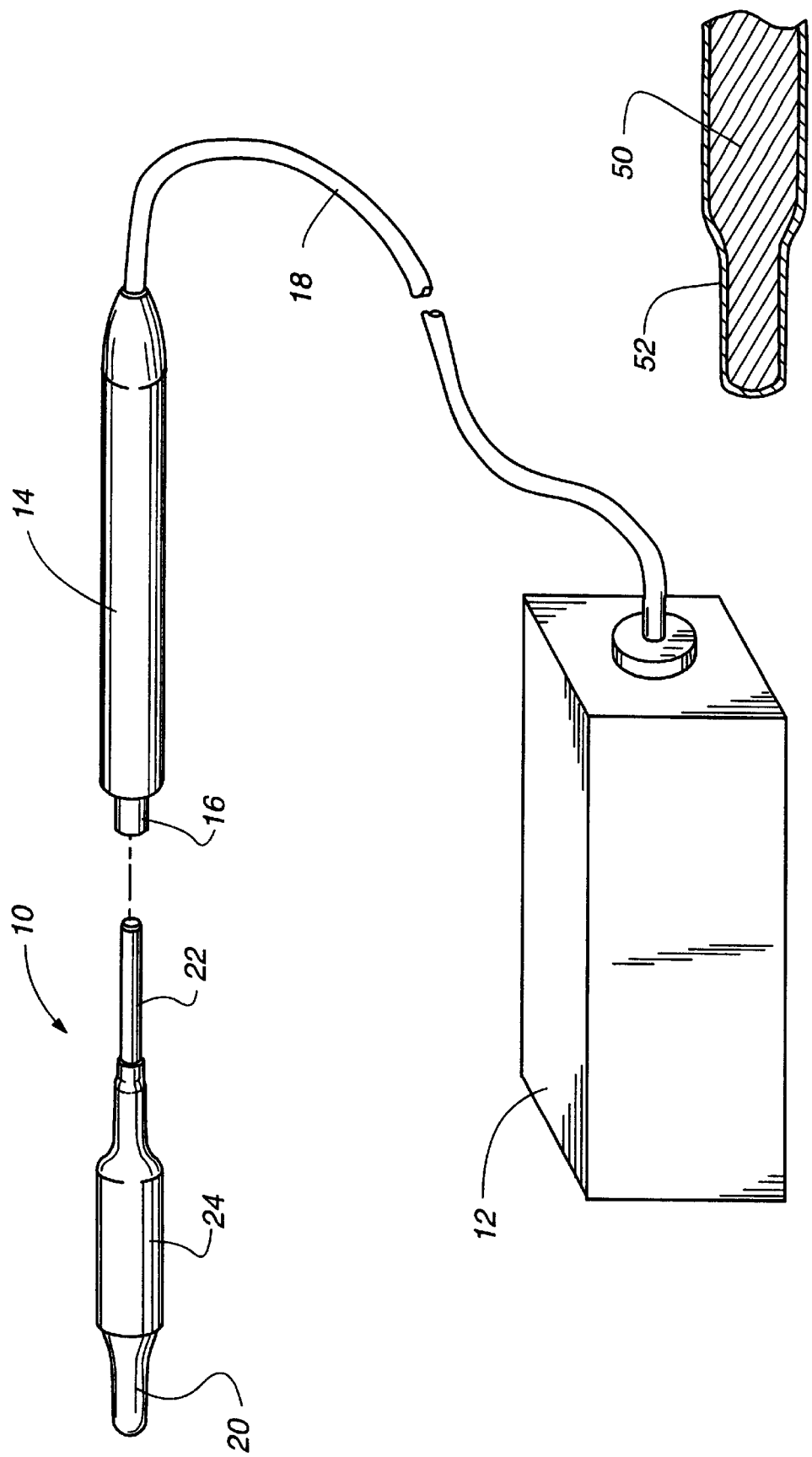

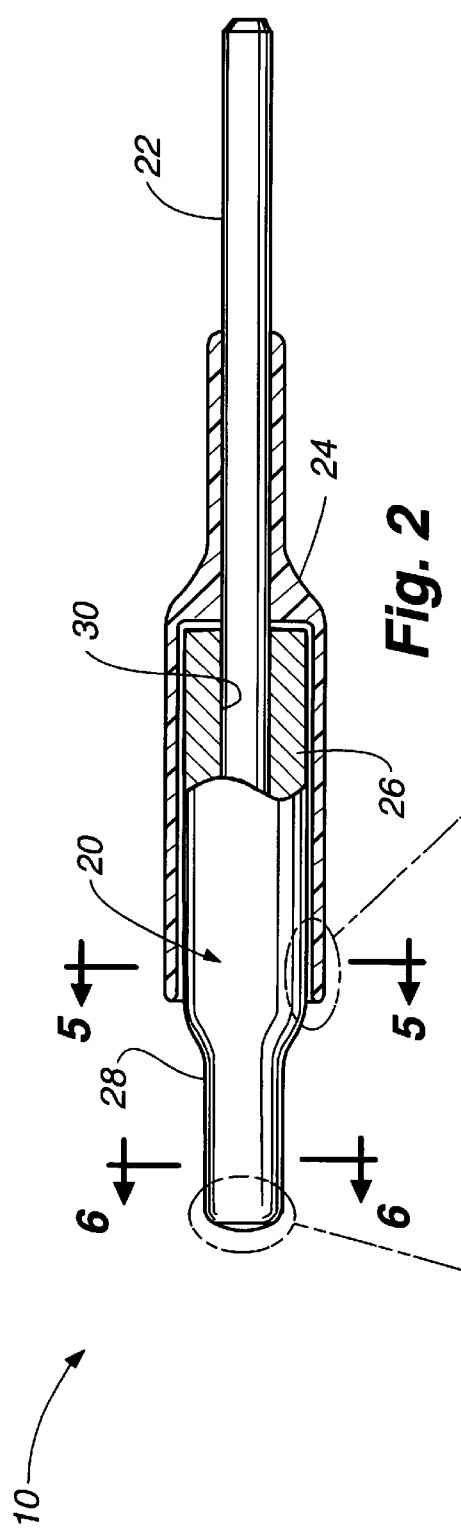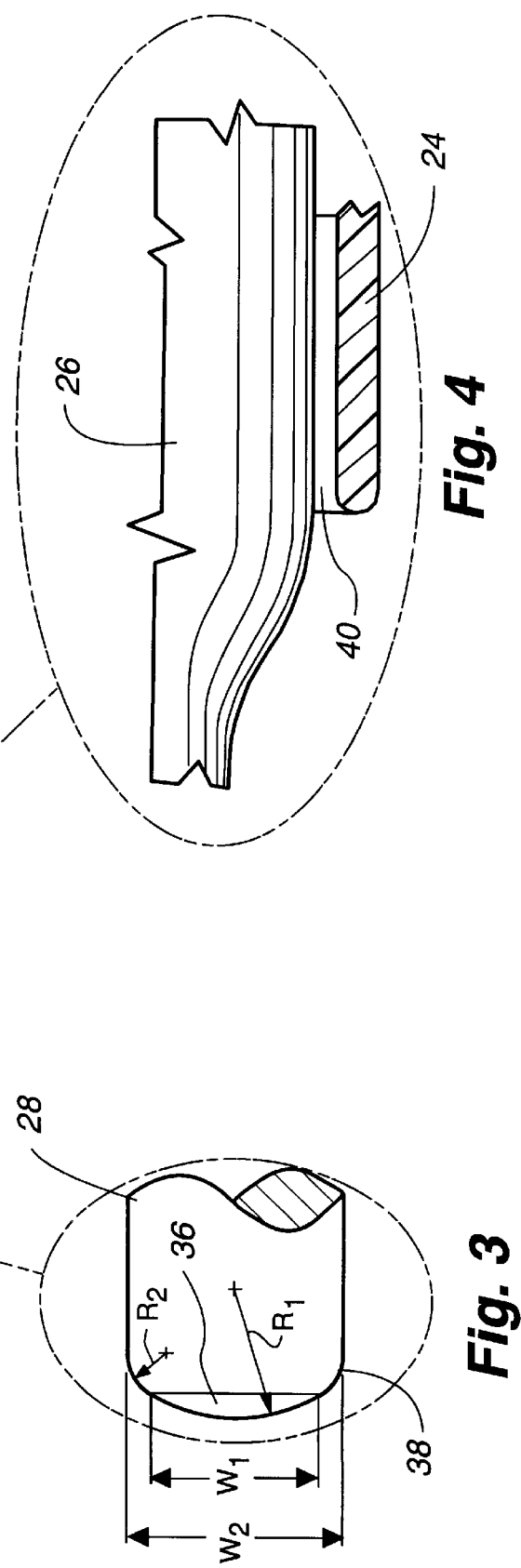

ELECTROSURGICAL ELECTRODE AND METHODS FOR ITS USE

CROSS-REFERENCE TO RELATED APPLICATIONS

This application claims priority from United States Provisional Patent Application No. 60/047,922, filed on May 29, 1997, and entitled "Electrosurgical Electrode and Methods for its Use," which is incorporated herein by reference.

The present invention relates generally to electrosurgical apparatus and methods for applying energy to tissue surfaces. In particular, the present invention relates to an electrode configuration which is suitable for applying radio-frequency energy to tissue and to fuse biological and other materials to tissue surfaces.

BACKGROUND OF THE INVENTION

The use of biological materials for the sealing of wounds and other defects in tissue as well as for the inhibition of tissue adhesion has been proposed. For example, the use of gelatin and collagen materials for closing wounds and/or creating anti-adhesive surfaces over tissue has been described in the prior art.

Of particular interest to the present invention, the use of radio-frequency (RF) energy to fuse biological materials to tissue surfaces has been suggested. While the use of conventional electrosurgical electrodes for performing such fusion has been proposed, the use of inert gas beam coagulators has often been preferred since there is no direct contact between the device and the underlying tissue and fusible material. Inert gas beam coagulators can be used to perform electrosurgery by transferring RF energy via a beam or stream of ionized inert gas which is directed to the underlying tissue. Thus, there is no direct contact of an electrode surface with the tissue and arcing and charring of the tissue/fusible material is minimized. A gelatin patch intended for fusion to lung tissue by the application of RF energy from an argon beam coagulator is available under the name RAPISEAL™ from Fusion Medical Technologies, Inc., of Mountain View, Calif.

While effective, the use of such inert gas beam coagulators for fusing a fusible material to tissue is problematic in several respects. Most significantly, many users have an initial difficulty in properly manipulating the handpiece of the electrosurgical instrument to apply the inert gas beam to the tissue. As there is no contact, there is no tactile feedback enabling the user to "feel" the fusion as it occurs. Moreover, inert gas beam coagulators are not as widely available in operating rooms as conventional electrosurgical coagulators, making their use somewhat more inconvenient.

The use of more conventional electrosurgical/electrocautery instruments would thus be beneficial in some respects. It would allow the user to contact the electrosurgical tip against the tissue/fusible material while applying energy thereto. Electrosurgical power supplies capable of supporting conventional electrosurgical tips are widely available and will thus both facilitate the procedure and reduce its overall cost.

The use of standard electrosurgical/electrocautery tips, however, is also problematic in certain respects. Many electrocautery electrodes cause arcing between the electrode tip and the underlying tissue. Such arcing is undesirable when fusing a biological material to tissue. Conventional electrocautery tip structures also have a tendency to stick to the underlying tissue, which tendency is exacerbated when an initially "loose" biological material is to be contacted and fused to the underlying tissue.

It would therefore be desirable to provide improved electrode tips for use in electrosurgical techniques, particularly for the fusion of biological and other materials to tissue. Such electrode tips should be capable of applying radio-frequency energy evenly and uniformly to the fusible materials, without significant arcing or charring. In particular, the electrode tips should apply the radio-frequency energy without sticking so that the positioning of the fusible material is not disturbed and damage to the tissue due to sticking does not occur. The electrode tips should be usable with conventional electrosurgical power supplies and should have geometries which permit both accessibility to the patient target sites as well as providing the proper energy density and flux for performing such fusion. In addition, it would be desirable if such electrosurgical tips were also usable for coagulation and other conventional electrosurgical procedures in addition to the particularly preferred fusion techniques relating to biological material.

In recent times, a split has developed between the medical communities in Europe and the United States. The desire to reduce the cost of medical supplies and, thus, medical procedures causes a portion of the medical community to embrace reusable medical supplies and instruments. Typically such items are sterilized with an autoclave, ethylene oxide gas, or other suitable technique, before re-use. Such reusable items must be able to withstand repeated sterilization through the autoclaving or other sterilization processes. In addition, reusable items need to be designed to withstand the wear and tear of repeated use. On the other hand, another portion of the medical community avoids reusable materials in order to reduce the likelihood of contaminating patients and medical personnel. In order to reduce such contamination, disposable items are used predominantly, or at least portions of the instruments and supplies are disposable. Some of the other reasons supporting reusables are that more expensive materials can be used in reusable supplies and instruments, when those more expensive materials have desirable characteristics, and also that the environmental impact of disposable items is so great.

U.S. Pat. No. 4,074,718 discloses an electrosurgical instrument with electrodes of increased thermal conductivity and a plurality of heat radiators attached thereto. Unfortunately, this reference did not recognize the importance of using bio-compatible materials, as several bio-compatible materials (silver and gold) were mentioned as interchangeable with non-compatible materials such as copper, aluminum, and beryllium. As to bio-compatibility at least, these materials are clearly not interchangeable, and they are probably not interchangeable in many other regards as well. In addition, the heat radiators on the electrode are poorly conceived, having a different effectiveness at different positional attitudes. Since the radiators rely on natural convection to remove heat from the electrode, the heat radiators will not function well when the electrode is oriented primarily vertically because the heat radiators will then be positioned above each other and heat convection away from the radiators will not easily occur. In addition, the embodiment with the ball electrode, shown in FIGS. 3 and 4, will not conduct heat effectively to the radiators since there will be a bottleneck in the smaller diameter region between the ball and the heat radiators. Similarly, the embodiment shown in FIGS. 1 and 2 will not conduct heat effectively to the heat radiators because the electrode is a blade electrode having a relatively small cross-sectional area relative to its length which restricts the heat flow.

U.S. Pat. No. 5,423,814 discloses a bipolar coagulation device intended for endoscopic applications. While there is a discussion in this reference of the need to use metals having high thermal conductivity for the electrode materials, the disclosure is of an alloy of such materials, namely an alloy comprised roughly of 80% copper, 15% silver and 5% phosphorous. Unfortunately copper is not bio-compatible, and it is believed that phosphorous is not as well. A particular electrode shape intended to enhance heat transfer away from the electrode tip to reduce tissue sticking is disclosed in FIG. 9a of this reference. The conical shape disclosed suffers from the drawback that there is no adequate heat reservoir toward which to transfer the heat away from the tip. In addition the width of the conical shape near the tip will reduce the surgeon's visibility. It is desirable that the electrode block the surgeon's view of the surgical site as little as possible.

It has generally been believed by those in the medical industry that silver, while high in thermal conductivity, is not bio-compatible. Apparently this belief arose because people referring to silver usually, if not always, are referring to sterling silver. Sterling silver is an alloy composed of 92.5% silver and 7.5% copper. Since copper is clearly not bio-compatible, testing of sterling silver has shown it is not bio-compatible. In addition, pure silver is almost never used in any applications since it is so soft or ductile. This is one reason why sterling silver is used rather than pure silver. In addition, pure (or nearly pure) silver is not commonly available through supply channels.

It is against this background, and the desire to solve the problems of the prior art, that the present invention has been developed.

SUMMARY OF THE INVENTION

The present invention provides an improved electrode assembly and methods for its use. The electrode assembly is suitable for use with conventional electrosurgical power supplies and is particularly suited for applying radio-frequency energy to fuse a fusible material to tissue. The energy applying tip of the electrode assembly is capable of applying energy to tissue and/or a fusible material in an even, uniform manner with little or no arcing between the electrode and the tissue. The electrode may be engaged and contacted directly against the tissue/fusible material with minimum or no sticking to the tissue and with reduced deep tissue damage. In addition, the electrode is useful for coagulation and other electrosurgical procedures in addition to fusing of the fusible material to tissue.

The present invention relates to an electrode for use in electrosurgery with an elongated electrode tip having a distal end and a thermal reservoir joining the electrode tip at a position spaced apart from the distal end, the thermal reservoir generally having a greater cross-sectional area than the cross-sectional area of the electrode tip to enhance the heat flow from the electrode tip to the thermal reservoir to reduce the temperature of the electrode tip during electrosurgery.

The present invention also relates to an electrode for use in electrosurgery with an electrode head at a distal end of the electrode, the head having a distal and a proximal end, wherein the head has a cross-sectional area at the distal end that is substantially equal to or less than the cross-sectional area of the head between the distal end and the proximal end. The electrode also includes an enlarged electrode base joined to the proximal end of the electrode head, wherein the electrode base generally has a substantially larger cross-sectional area than the electrode head.

The present invention also relates to an electrode for use in electrosurgery, with an electrode composed of a material with a purity level of over 95% by weight, the material coming from the group consisting of silver, gold, and any alloy of silver and gold which has a thermal conductivity of 169 to 172 BTU/(hour·foot·° Fahrenheit), wherein the remainder of the electrode is composed of a bio-compatible material.

The present invention is also related to an electrode for use in electrosurgery with an electrode composed primarily of a bio-compatible material, the material having sufficiently high thermal conductance to minimize charring tissue and adhesion of tissue to the electrode.

The present invention is also related to an electrode for use in electrosurgery with an electrode composed of at least 90% silver, wherein the remainder is a bio-compatible material, and further wherein the silver has been work-hardened by at least 10%.

The present invention is also related to an electrode for use in electrosurgery with an electrode core composed of a material having greater thermal conductivity than stainless steel and an electrode coating surrounding the electrode core, the coating composed primarily of silver, wherein the remainder of the coating is a bio-compatible material.

The present invention is also related to an electrode assembly with a core element having a proximal end, a distal end, a shank region, and a tip extension, wherein the tip extension has an average width in the range from 0.1 mm to 15 mm, a distal tip, and a length at least equal to the tip extension width, and wherein the shank region has a cross-sectional area which is primarily equal to or greater than that of the tip extension and a length at least equal to the tip extension diameter. The electrode assembly also includes a connector electrically coupled to the proximal end of the shank region and an insulating sleeve over the shank region.

The present invention is also related to a method for fusing a fusible material to tissue. The method includes providing an electrode having an energy-applying tip, wherein the tip has a curved surface, placing the fusible material over tissue, energizing the electrode with radio-frequency energy and engaging the curved surface of the electrode tip against the fusible material while the electrode is energized, whereby the fusible material fuses to the tissue.

The present invention is also related to a kit. The kit includes an electrode assembly, instructions for use setting forth a method as described above, and a package holding the electrode assembly and the instructions.

BRIEF DESCRIPTION OF THE DRAWINGS

FIG. 1 schematically illustrates an electrosurgical system comprising a conventional electrosurgical power supply and an electrode assembly according to the present invention.

FIG. 2 is a detailed view of the electrode assembly of FIG. 1, shown in partial section.

FIG. 3 is a detailed view of the distal tip of the electrode assembly of FIG. 2.

FIG. 4 is a detailed view of the air gap between the insulating sleeve and the core element of the electrode assembly of FIG. 2.

FIG. 10 is a sectional view of another embodiment of an electrode according to the present invention.

DESCRIPTION OF THE SPECIFIC EMBODIMENTS

Figure 7:
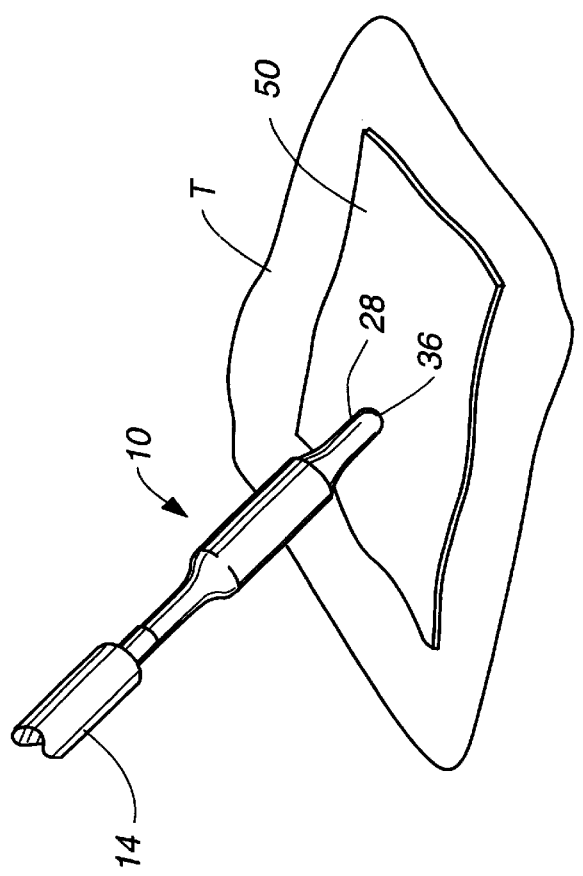
FIG. 7 illustrates use of the electrosurgical system of FIG. 1 for applying radio-frequency energy to fuse a patch material to tissue according to a method of the present invention.

Referring to FIG. 1, an electrode assembly 10 constructed in accordance with the principles of the present invention can be used together with a conventional electrosurgical generator or power supply 12 having a handpiece 14 with a distal connector 16 and a cable 18 connecting the handpiece to the power supply. The electrosurgical power supply 12 may be any one of a variety of power supplies intended for electrosurgical cutting and/or coagulation available from suppliers such as ConMed Corp., Utica, N.Y., and Valleylab, Inc., Boulder, Colo. Such power supplies are generally capable of operating at radio-frequencies of about 500 kHz and at power levels from 1 W to 300 W. The methods of the present invention are preferably performed at relatively low power levels, typically at power levels in the range from 10 W to 50 W. A particular suitable power supply is commercially available from ConMed Corp., under the name Excalibur Plus PC™.

Referring now also to FIG. 2, the electrode assembly 10 includes an electrode or core element 20, a connector 22 adapted to plug into the connector 16 on handpiece 14, and an insulating sleeve 24. The core element 20 is formed from an electrically and thermally conductive material, such as silver of a purity level of 99.9% by weight. The core element includes a generally cylindrical shank region 26 and a generally cylindrical head or tip extension 28 extending distally from a distal end of the shank region. As used herein, distal refers to the end of an object furthest from the electrosurgical generator 12, while proximal refers to the end of an object closest to the electrosurgical generator 12. As illustrated, the core element 20 comprises a continuous structure where the tip extension 28 tapers to a smaller cross-sectional area from the shank region 26. The dimensions and materials of the core element 20 are generally as set forth herein. The connector 22 is received in an axial receptacle 30 formed along the center line of the core element 20. Typically, the connector 22 will be joined by a friction fit, but electrically conductive adhesives and/or welding could also be used. Any structure which provides mechanical and electrical integrity will be suitable.

Typically, the connector 22 will be formed separately from the core element 20 and joined thereto, usually by a friction fit in a receptacle formed in the shank region 26. Providing a separate connector is advantageous since it permits the core element to be formed from a material having particular characteristics suitable for the core element (as described below) while the connector can be formed from a material which is suitable for inserting into the handpiece of a conventional electrosurgical power supply. Typically, the connector will be composed of a stainless steel, such as stainless steel 303.

The configuration of the distal tip of tip extension 28 is illustrated in detail in FIG. 3. The distal tip of the tip extension may be "rounded". By "rounded," it is meant that the tip will terminate in a continuously curved surface. Most simply, the continuously curved surface could be a portion of a spherical, but it could also be ovoid or even be asymmetrically curved about one or more axes. It is preferred that the tip recess along continuous (generally non-disrupted) curved lines so that its periphery is recessed back from the center of the tip in a smooth manner. Any geometry with an increasing cross-sectional area when moving from the distal to the proximal end of the core element should work. In the embodiment shown, the distal tip comprises an end region 36 having a spherical surface with a radius of curvature $R_1$ which may typically be in the range from 3 mm to 5 mm, preferably being about 3.3 mm. The end region 36 has a width $W_1$, typically a diameter, in the range from 2 mm to 6 mm, typically being about 3 mm. A transition region 38 having a minor radius of curvature $R_2$ in the range from 1 mm to 1.5 mm is disposed concentrically about the end region 36. The width $W_2$ of the outer periphery of the transition region 38 is equal to the diameter of the tip extension 28 and is in the range from 4 mm to 5 mm, typically being about 4.6 mm. Thus, the transition region 38 has an annular width in the range from about 0.5 mm to 0.75 mm. It has been found that the radius of curvature of the end region 36 contributes to the ability of the electrode assembly 10 to deliver radio-frequency energy at the desired fluxes without significant arcing or adhesion to underlying tissues. The ability to provide the relatively narrow diameter tip extension 28 while providing the desired radius of curvature of the end 30 is further facilitated by providing the transition region having a lesser radius of curvature $R_2$. Thus, the distal tip of the distal extension 28 has a central region with the first radius of curvature that is surrounded by a transition region having a different minor radius of curvature to provide the desired energy transfer characteristics. It is believed that these different regions provide different flux densities in the electrical energy applied to the tissue. Thus, the surgeon could selectively manipulate the handpiece to orient different portions of the tip toward the tissue to achieve different electrosurgical effects. It would be possible to have an end with a smaller radius of curvature than the transition region, or any other combination, including no transition region. In addition, the curved shape could be approximated by providing a plurality of small flat surfaces angled slightly relative to each other to achieve a curved effect.

Each of the dimensions provided above is for the embodiment shown. This invention is equally applicable to laparoscopic, dental, and other applications where it may be desirable to have a much smaller (or possibly larger, in some circumstances) electrode. It is the relative dimensions and not the absolute dimensions that would be relevant in such other applications. For example, it is possible that the overall width of the electrode may be as small as 0.1 mm and as large as 15 mm.

Figure 6:
FIG. 6 is a sectional view of a head portion of the electrode assembly, taken along line 6—6 of FIG. 2.
Figure 5:
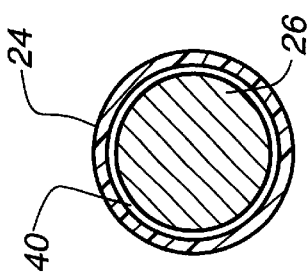
FIG. 5 is a sectional view of a shank portion of the electrode assembly, taken along line 5—5 of FIG. 2.

The tip extension 28 has an average width, typically a diameter in the case of tip extensions having circular cross-sections, in the range from 3 mm to 5 mm. The distal tip of the tip extension 28 is rounded and has a length of at least about 5 mm, typically being in the range from 5 mm to 15 mm. In order to enhance heat transfer away from the tip extension 28, the shank region 26 of the core element will have a cross-sectional area which is larger than that of the tip extension 28, preferably being in the range from two times to eight times that of the tip extension 28, as seen relatively in FIGS. 5 and 6. The shank region 26 will also have a length of at least about 15 mm, preferably being in the range from 20 mm to 50 mm. The shank region 26 is thus able to act as a thermal sink or reservoir to draw away heat from the tip extension 28 while the tip extension 28 itself remains sufficiently small to access desired target sites, provide sufficient visibility of the target site, and display the desired energy transfer properties.

The electrode assembly 10 also includes the insulating sleeve 24 formed over at least the shank region 26 of the core element 20. Preferably, the insulating sleeve 24 will be formed over only the shank region 26 of the core element 20 (and optionally a distal portion of the connector), leaving the tip extension 28 free from insulation. The insulating sleeve 24 will usually be formed of a polymeric material having a high dielectric strength and ability to withstand relatively high temperatures. The material may preferably have a dielectric strength equal to or greater than 200 volts/mil. Suitable materials include polyphenylsulfone, an amorphous polymer with high thermal stability and mechanical strength, polyarylethersulfone, such as Radel™ or Radel-R™ (available from Amoco Polymers, Alphanette, Ga.), polysulfone, such as Udel, polyetherimide, such as Ultem, polycarbonate, such as Lexan, or any other suitable material. As shown in FIG. 1, the insulating sleeve 24 may preferably have a reduced diameter neck at a proximal end thereof so that the neck portion can fit into the distal connector 16 of the handpiece 14.

Referring now to FIG. 4, an air gap 40 is preferably provided beneath the insulating sleeve 24 and around the exterior surface of the shank region 26 of the core element 20. The air gap preferably has a width in the range from 0.1 mm to 0.5 mm, usually being about 0.4 mm. The air gap is primarily useful to facilitate mounting and/or removal of the sleeve 24 from the core element 20 in order to clean the electrode assembly. The air gap additionally may enhance the transfer of heat away from the shank region 26 which in turn enhances the heat conduction away from the tip extension 28. The ability to remove heat from the tip extension 28 is also an important aspect of lessening adhesion of the tip to the tissue/fusible material.

The core element 20 is composed of a material having both high electrical and thermal conductivities and which is biologically compatible (bio-compatible) when used to apply radio-frequency energy to tissue and/or fusible materials. The term bio-compatible is used to refer to materials meeting the ISO 10993 standard for "Biological Evaluation of Medical Devices." Preferably, the electrode core element 20 will be formed from a substantially pure metal having the desired electrical and thermal characteristics. Suitable metals include silver and gold, or alloys of silver and gold. Particularly preferred are substantially pure silver electrode cores, preferably having a purity of at least 90% by weight, more preferably of at least 99% by weight, and even more preferably, of 99.9% by weight. The remainder of the electrode core would be composed of another bio-compatible metal. Alternatively, it is possible to employ a variety of composite, laminated, and coated structures as the electrode core. For example, it would be possible to employ an aluminum central core 50 which is coated with a coating 52 of silver, gold, or tungsten, preferably silver, as shown in FIG. 10. The coating 52 of the outer metal should be relatively thick, typically having an annular thickness of at least about 0.5 mm, preferably at least about 1 mm. The central core 50 should be composed of a material having higher thermal conductivity than stainless steel, such as aluminum or copper. Even less preferably, carbon-coated stainless steel electrodes, such as those described in U.S. Pat. No. 4,074,718, could be used for performing the methods of the present invention. Such carbon-coated electrodes, however, do not display the optimum performance characteristics of the preferred pure metal, e.g. pure silver, electrodes. It is known that stainless steel has a thermal conductivity in the range of 9 to 13 BTU/(hour·foot·° Fahrenheit), so materials with significantly greater thermal conductivities should preferably be employed in the present invention as electrode materials. This may include using silver, which has a thermal conductivity in the range of 209 to 240 BTU/(hour·foot·° Fahrenheit).

One issue with such high purity levels of silver is the ductile nature of pure (or nearly pure) silver. Because of this, it is preferred to cold work-harden the silver by at least a 10% reduction in area in a conventional manner. Once work-hardened in this manner, the silver can be formed into a usable instrument such as the electrode of the present invention. Even more preferable is silver that has been work-hardened by a 50% reduction in area. Work-hardening has been found to not substantially affect the thermal conductivity of the material while making it much more resistant to damage.

The ability to transfer heat away from the tip extension 28 of the core element 20 is an important advantage of the electrode assemblies of the present invention. The use of silver or gold (or other thermally conductive materials) as the core material as well as the shape of the electrode are primarily responsible for the improved heat transfer. The heat transfer is further enhanced by the enlarged cross-sectional area of the shank region 26 of the core element 20. This enlarged cross-sectional area of the shank region 26 helps to promote the flow of heat away from the distal tip of the tip extension 28, since the heat flow is proportional to the thermal conductivity of the metal, to the cross-sectional area of the region of interest, and to the temperature differential across the region of interest. The heat flow is inversely proportional to the length of the region of interest. As can be appreciated, this invention directly addresses the thermal conductivity and the cross-sectional area variables of the heat flow equation. The heat transfer capability is possibly still further enhanced by configuring the insulating sleeve 24 to leave a small air gap between the inner surface of the sleeve and the outer surface of the shank region 26. Usually, this is achieved by providing an insulating sleeve with an inner diameter which is slightly larger than the outer diameter of the shank region 26, typically being sufficiently large to provide an annular air gap in the range from 0.1 mm to 0.5 mm. It is possible that the shank region could have a small neck therein. Such a design may still achieve the desired effect of the present invention since the portion of the shank region on the distal side of the neck may adequately act as the thermal reservoir. Similarly, the neck extension may have a small neck therein.

A factor controlling the overall width of the tip of the electrode is the need to preserve the surgeon's view of the surgical site while performing electrosurgery with the electrode. For this reason, the electrode tip is limited to a reasonable width and is connected to a thermal reservoir (the shank region) not too far away therefrom. In this manner, the visibility of the surgical site is maintained.

It can be appreciated that the silver or gold electrodes of the present invention can be autoclaved or subjected to other sterilization techniques and thus are suitable as reusable instruments. In addition, the particular insulating sleeves discussed above as well as the connector may be sterilized as well.

Referring now to FIG. 7, a fusible patch 50, which may be gelatin, collagen or other biological or non-biological fusible material, is placed over a target tissue surface T.

Specific fusible materials and tissue surfaces include a gelatin patch sold under the name RAPISEAL™ patch by Fusion Medical Technologies of Mountain View, Calif. After placement of the patch 50, the user manipulates electrosurgical handpiece 14 to engage the end region 36 of the tip extension 28 of the core element against the patch 50. Radio-frequency energy is applied through the electrode assembly 10 and into the interface of the patch 50 and tissue surface T in order to fuse the patch material to the underlying tissue. The power supply will generally be operated within the power ranges set forth above. The electrode assembly 10 will be engaged directly against the patch material 50 and held against the patch material until the material has visibly fused to the tissue. The entire patch area 50 may be contacted and fused. Alternatively, only portions of the patch material may be contacted and "tacked" to the underlying tissue.

Figure 8:
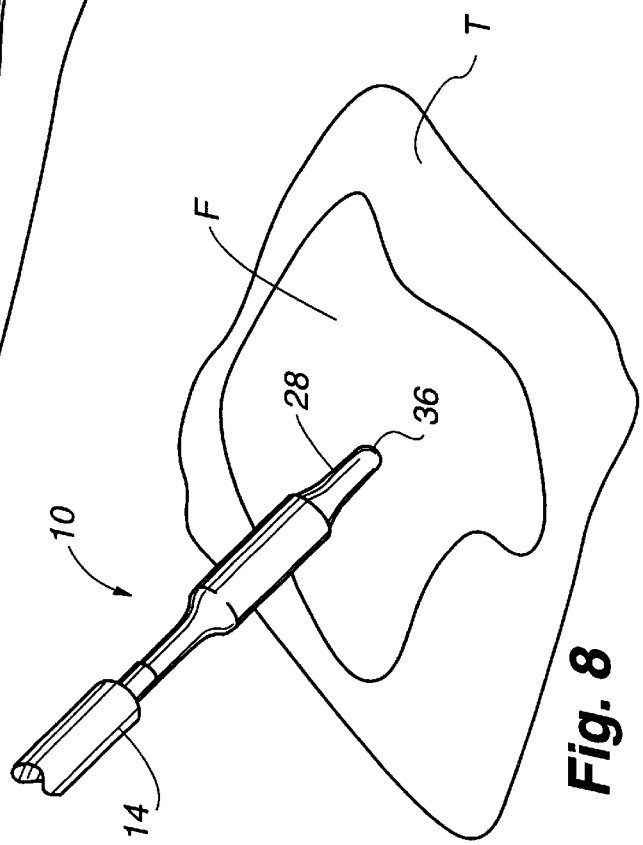
FIG. 8 illustrates use of the electrosurgical system of FIG. 1 for applying radio-frequency energy to a gel material to fuse said material to tissue according to a method of the present invention.

Referring now to FIG. 8, a flowable fusible material F may be applied to tissue T using a syringe, spatula, or other applicator. Suitable flowable materials may include collagen or gelatin in liquid or gel form. After the flowable material is applied, the handpiece 14 of the electrosurgical system will be used to engage the end region 36 of the electrode assembly 10 against the flowable material. Energy will be applied as described above in order to fuse the flowable material left to the underlying tissue. Generally, it will be necessary to apply energy to the entire surface area of the flowable material left in order to immobilize that material to the tissue in a desired fashion.

As can be seen, the methods according to the present invention for fusing a fusible material to tissue include providing an electrode having an energy-supplying tip, at least a portion of which may be rounded as defined above. Preferred electrodes are described above in connection with the electrode assembly. The fusible material is placed over tissue, and the electrode energized with radio-frequency energy. The spherical surface of the energized electrode is then engaged against the fusible material, whereby the fusible material fuses to the tissue. Usually, the fusible material is a biological material, such as a protein, carbohydrate, or combination thereof, but it may also be a synthetic polymer. An exemplary fusible material comprises gelatin. The fusible material may be in a solid form, such as a film, sheet, or patch, prior to placement and application of radio-frequency energy. Alternatively, the fusible material may be in a flowable form, such as a liquid or gel, prior to placement and fusion. The energizing step typically comprises applying a radio-frequency current between the electrode and the tissue, typically at a power level in the range from 5 watts (W) to 100 W, preferably from 10 W to 45 W. Such energy is usually applied using a conventional electrosurgical power supply in a monopolar manner.

Figure 9:
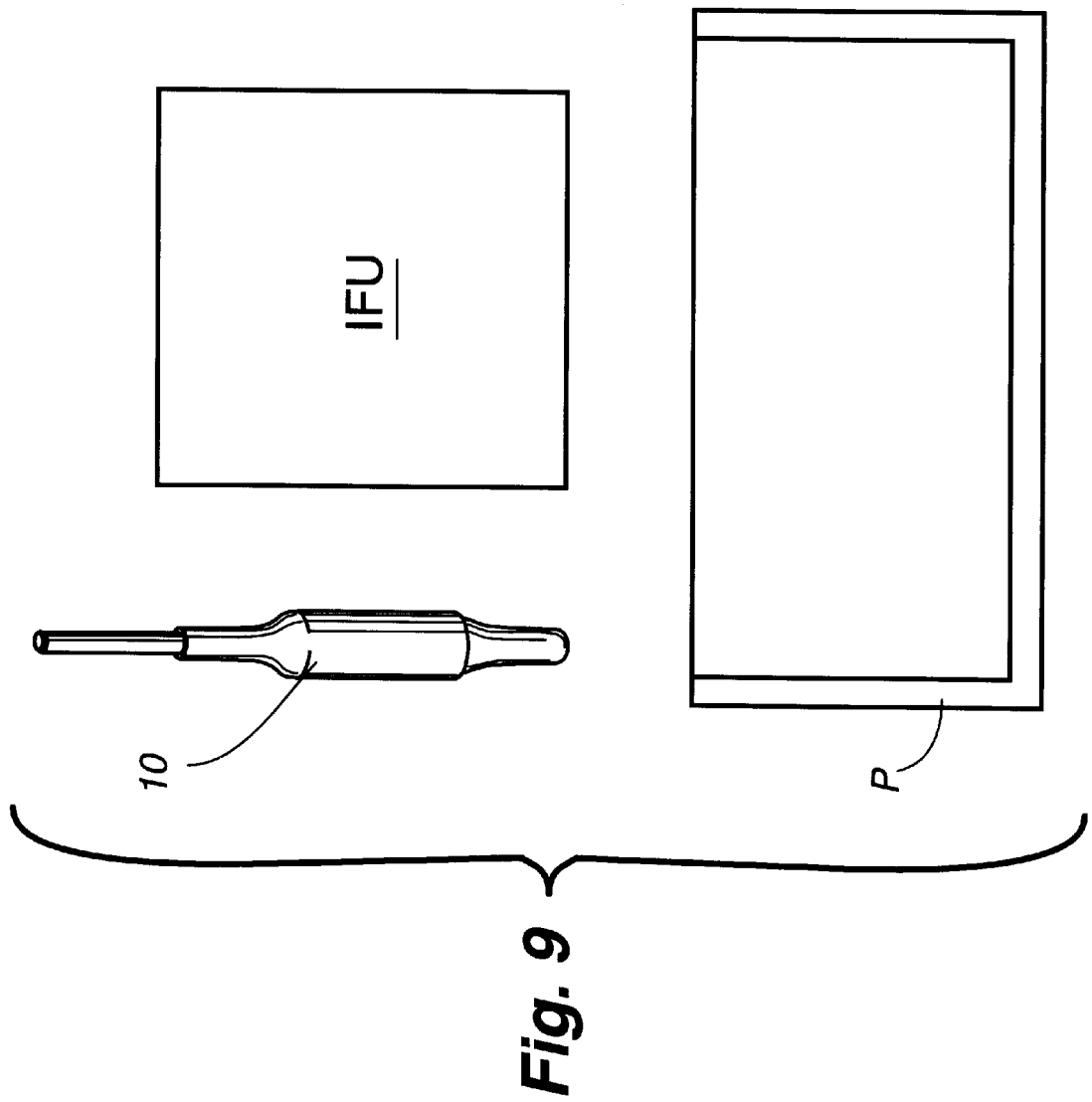
FIG. 9 illustrates a kit according to the present invention comprising an electrode assembly, a package, and instructions for use.

Any electrode assembly of the present invention may be packaged together with instructions for use (IFU) in a kit, as shown in FIG. 9. A conventional package, which may be a pouch P or any other suitable package, such as a tray, box, tube, or the like, may be used to contain the electrode assembly 10 and IFU, where the IFU may be printed on a separate sheet and/or may be printed on the packaging itself. Optionally, but not necessarily, the electrode assembly 10 may be sterilized within the package, e.g. by radiation or ethyleneoxide. The instructions will set forth any of the aspects of the method of the present invention described above. Preferably, the electrode will be silver and will be maintained in a non-oxidative environment, e.g. in an inert gas, within the package.

While the above is a complete description of the preferred embodiments of the invention, various alternatives, modifications, and equivalents may be used. Therefore, the above description should not be taken as limiting the scope of the invention which is defined by the appended claims.

The invention claimed is:

1. An electrode for use in electrosurgery, comprising:
    an elongated electrode tip having a distal end and a proximal end, the proximal end having a cross-sectional area that is greater than or equal to the cross-sectional area of any point on the electrode tip other than the proximal end, and the distal end having a cross-sectional area that is less than or equal to the cross-sectional area of any point on the electrode tip other than the distal end, a distance between the distal end and the proximal end of the electrode tip being less than three times a diameter of a central point on the electrode tip between the distal end and the proximal end;
    a thermal reservoir joining the electrode tip at the proximal end of the electrode tip, the thermal reservoir generally having a greater cross-sectional area at each part of the thermal reservoir than the cross-sectional area of the electrode tip to enhance the heat flow from the electrode tip to the thermal reservoir to reduce the temperature of the electrode tip during electrosurgery;
    wherein both the electrode tip and the thermal reservoir are composed of a thermally conductive material having a thermal conductivity greater than about 169 BTU/(hr·ft·° F.).

2. An electrode for use in electrosurgery, comprising:
    an electrode head at a distal end of the electrode, the electrode head having a distal end and a proximal end, wherein the electrode head has a cross-sectional area at the distal end that is substantially equal to or less than the cross-sectional area of the electrode head between the distal end and the proximal end; and
    an enlarged electrode base joined to the proximal end of the electrode head, wherein the electrode base generally has a substantially larger cross-sectional area than the electrode head;
    wherein both the electrode head and the electrode base are composed of a thermally conductive material having a thermal conductivity greater than about 169 BTU/ (hr·ft·° F.).

3. An electrode as defined in claim 2, wherein the electrode head is generally cylindrical.

4. An electrode as defined in claim 2, wherein the electrode base is generally cylindrical.

5. An electrode as defined in claim 2, wherein each of the electrode head and electrode base are generally cylindrical.

6. An electrode as defined in claim 2, wherein the electrode is monopolar.

7. An electrode for use in electrosurgery, comprising:
    an electrode composed of a material with a purity level of over 95% by weight, the material coming from the group consisting of silver, gold, and any alloy of silver and gold, wherein the remainder of the electrode is composed of a bio-compatible material.

8. An electrode as defined in claim 7, wherein the electrode includes a thermal reservoir spaced apart from a distal tip of the electrode.

9. An electrode as defined in claim 8, wherein the thermal reservoir has a greater cross-sectional area than the distal tip of the electrode.

10. An electrode as defined in claim 9, wherein the cross-sectional area of the electrode remains substantially constant or increases from the distal tip to the thermal reservoir.

11. An electrode as defined in claim 7, wherein the purity level is over 97%.

12. An electrode as defined in claim 7, wherein the purity level is 99.95 or greater.

13. An electrode for use in electrosurgery, comprising:
an electrode composed of at least 90% silver, wherein the remainder is a bio-compatible material, and further wherein the silver has been work-hardened by at least 10%.

14. A monopolar electrode for use in electrosurgery, comprising:
an electrode head at a distal end of the electrode, the head having a distal and a proximal end, wherein the head has a cross-sectional area at the distal end that is substantially equal to or less than the cross-sectional area of the head between the distal end and the proximal end; and
a thermal reservoir joining the electrode head at a position spaced apart from the distal end, the thermal reservoir generally having a greater cross-sectional area than the cross-sectional area of the electrode head to enhance the heat flow from the electrode tip to the thermal reservoir to reduce the temperature of the electrode head during electrosurgery;
wherein the electrode head and thermal reservoir are composed of at least 90% silver by weight, with the remainder being a bio-compatible material, wherein the silver has been work-hardened by at least 10%.

15. An electrode for use in electrosurgery, comprising:
an electrode core composed of a material having greater thermal conductivity than stainless steel; and
an electrode coating surrounding the electrode core, the coating composed primarily of a metal selected from a group consisting of gold, tungsten and silver, wherein the remainder of the coating is a bio-compatible material.

16. An electrode as defined in claim 15, wherein the electrode core is composed of aluminum, copper, or an alloy thereof.

17. An electrode assembly comprising:
a core element having a proximal end, a distal end, and a shank region that is located between said proximal end and said distal end of said core element;
a tip extension located at said distal end of said core element;
a distal tip located at a distal end of said tip extension;
said tip extension having an average width in a range of from about 0.1 mm to about 15 mm, and a length at least equal to said average width of said tip extension;
said shank region having a cross-sectional area equal to or greater than a cross-sectional area of said tip extension;
said shank region having a length at least equal to said average width of said tip extension;
said core element being composed of a thermally conductive material having a thermal conductivity greater than about 169 BTU/(hr·ft·° F.);
a connector electrically coupled to said proximal end of said core element; and
an insulating sleeve located over said shank region;
said insulating sleeve having an internal width that is sufficiently large to form air gap between an inner surface of said insulating sleeve and an outer surface of said shank region.

18. An electrode assembly as defined in claim 17 wherein the said gap has an average width in a range from about 0.1 mm to about 0.5 mm.

* * * * *